(12) United States Patent
Mendrok-Edinger

(10) Patent No.: US 12,351,690 B2
(45) Date of Patent: Jul. 8, 2025

(54) COMPOSITIONS COMPRISING SPECIFIC HYPERBRANCHED COPOLYMERS TOGETHER WITH 1,3-PROPANDIOL AND N-HYDROXYOCTANAMIDE

(71) Applicant: DSM IP ASSETS B.V., Heerlen (NL)

(72) Inventor: Christine Mendrok-Edinger, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 486 days.

(21) Appl. No.: 17/599,791

(22) PCT Filed: Mar. 31, 2020

(86) PCT No.: PCT/EP2020/059102
§ 371 (c)(1),
(2) Date: Sep. 29, 2021

(87) PCT Pub. No.: WO2020/201273
PCT Pub. Date: Oct. 8, 2020

(65) Prior Publication Data
US 2022/0135747 A1    May 5, 2022

(30) Foreign Application Priority Data
Apr. 1, 2019 (EP) .................... 19166543

(51) Int. Cl.
| | | |
|---|---|---|
| *C11D 3/20* | (2006.01) | |
| *A61K 8/34* | (2006.01) | |
| *A61K 8/42* | (2006.01) | |
| *A61K 8/88* | (2006.01) | |
| *A61Q 5/02* | (2006.01) | |
| *A61Q 5/12* | (2006.01) | |
| *A61Q 17/00* | (2006.01) | |
| *C08G 83/00* | (2006.01) | |
| *C11D 3/30* | (2006.01) | |
| *C11D 3/32* | (2006.01) | |
| *C11D 3/37* | (2006.01) | |
| *C11D 3/43* | (2006.01) | |
| *C11D 7/26* | (2006.01) | |
| *C11D 7/32* | (2006.01) | |

(52) U.S. Cl.
CPC ............ *C08G 83/005* (2013.01); *A61K 8/345* (2013.01); *A61K 8/42* (2013.01); *A61K 8/88* (2013.01); *A61Q 5/02* (2013.01); *A61Q 5/12* (2013.01); *A61Q 17/005* (2013.01); *C08G 83/006* (2013.01); *C11D 3/2041* (2013.01); *C11D 3/30* (2013.01); *C11D 3/32* (2013.01); *C11D 7/261* (2013.01); *C11D 7/3209* (2013.01); *C11D 7/3263* (2013.01); *A61K 2800/544* (2013.01)

(58) Field of Classification Search
CPC ........... C11D 3/2041; C11D 3/30; C11D 3/32; C11D 7/3209; C11D 7/3263; C11D 7/261
USPC ........ 510/119, 130, 123, 501, 502, 504, 505
See application file for complete search history.

(56) References Cited

U.S. PATENT DOCUMENTS

| | | |
|---|---|---|
| 8,951,509 B2 | 2/2015 | Beumer et al. |
| 2013/0251659 A1 | 9/2013 | Derks et al. |
| 2014/0348771 A1 | 11/2014 | Beumer et al. |

FOREIGN PATENT DOCUMENTS

| | | | |
|---|---|---|---|
| CN | 102065833 | 5/2011 | |
| CN | 104619309 | 5/2015 | |
| CN | 104640931 | 5/2015 | |
| EP | 2883533 A1 * | 6/2015 | ............ A61K 8/342 |
| EP | 2895141 | 7/2015 | |
| EP | 2895560 | 7/2015 | |
| JP | 2009-528391 | 8/2009 | |
| JP | 2009-528439 | 8/2009 | |
| JP | 2011-524883 | 9/2011 | |
| JP | 2016-527340 | 9/2016 | |
| KR | 10-1641498 | 7/2016 | |

OTHER PUBLICATIONS

First Official Action, CN Application No. 202080024992.5, Nov. 18, 2022.
International Search Report for PCT/EP2020/059102, mailed Apr. 21, 2020, 3 pages.
Written Opinion of the ISA for PCT/EP2020/059102, mailed Apr. 21, 2020, 7 pages.
Notice of Reasons for Rejection, JP Application No. P2021-556336, Jun. 4, 2024.

* cited by examiner

*Primary Examiner* — Gregory R Delcotto
(74) *Attorney, Agent, or Firm* — Nixon & Vanderhye, P.C.

(57) ABSTRACT

The present invention relates to a composition comprising a specific hyperbranched copolymer (HBC) of the monomers dodecenyl succinic acid anhydride, diisopropanol amine and bis-dimethylaminopropyl amine and the compound 1,3-propandiol and/or N-hydroxyoctanamide. It has been found that said hyperbranched copolymer synergistically enhances the antimicrobial action of a 1,3-propanediol and/or N-hydroxy-octanamide.

19 Claims, No Drawings

COMPOSITIONS COMPRISING SPECIFIC HYPERBRANCHED COPOLYMERS TOGETHER WITH 1,3-PROPANDIOL AND N-HYDROXYOCTANAMIDE

This application is the U.S. national phase of International Application No. PCT/EP2020/059102 filed 31 Mar. 2020, which designated the U.S. and claims priority to EP patent application Ser. No. 19/166,543.9 filed 1 Apr. 2019, the entire contents of each of which are hereby incorporated by reference.

TECHNICAL FIELD

The present invention relates to the field of antimicrobial agents, particularly in the field of cosmetic compositions.

BACKGROUND OF THE INVENTION

Antimicrobial agents are known ingredients to stabilizes compositions, particularly cosmetic compositions, by reducing the growth of microorganisms. The reduction of growth of microorganisms is essential for the consumers safety and health when using a cosmetic product. By reducing the growth of microorganisms, the shelf life of a cosmetic product can be increased. As the use of certain antimicrobial agents are under public discussions a reduction of antimicrobial agents is a strong desire, particularly in the cosmetic industry.

EP 2 794 729 B1 disclose the preparation of specific hyperbranched polyesters which can be used as flocculants in paper production and in dishwater detergents.

EP 2 296 619 B1 discloses that specific hyperbranched copolymers have an advantageous effect in a shampoo for increasing the volume of hair.

1,3 propanediol and N-hydroxyoctanamide are compounds which are known to be used as an active antimicrobial adjuvant in cosmetic compositions.

SUMMARY OF THE INVENTION

Therefore, the problem to be solved by the present invention is to offer a composition with enhanced antimicrobial properties.

It has been surprisingly found that the composition of claim 1 is able to solve this problem. It has been particularly observed that a specific hyperbranched copolymer is able to enhance the antimicrobial action of antimicrobial agents used particularly in cosmetic compositions. This effect is a synergistic effect of the specific hyperbranched copolymer on to the antimicrobial effect of an antimicrobial agent. This surprising finding is very advantageous as this invention can lead to higher stability, longer shelf life, respectively, to the reduction of antimicrobial agents in compositions, particularly in cosmetic compositions, by, nevertheless, maintaining the antimicrobial properties.

Further aspects of the invention are subject of further independent claims. Particularly preferred embodiments are subject of dependent claims.

DETAILED DESCRIPTION OF THE INVENTION

In a first aspect the present invention relates to a composition comprising
 a) a hyperbranched copolymer (HBC) of the monomers
  (i) dodecenyl succinic acid anhydride
  (ii) diisopropanol amine
  (iii) bis-dimethylaminopropyl amine
   having terminal groups of the formula

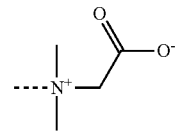

and having a molecular weight Mn of between 1200 and 4000 g/mol; and
 b) 1,3-propanediol and/or N-hydroxyoctanamide.

The term "molecular weight Mn" stands for the number average molecular weight.

The term "preparation" or "formulation" is used in this document as equivalent to the term "composition".

The term "antimicrobial agent" is used in this document for an organic chemical substance which reduces the growth of microorganisms. However, monohydroxy-$C_1$-$C_6$ alkanes, such as methanol, ethanol, propanol or iso-propanol, for this invention, are not considered to be antimicrobial agents. For sake of clarity, it is worthwhile that antioxidants are not to be regarded as antimicrobial agents.

1,3 propanediol has the formula

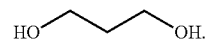

1,3 propanediol is commercially readily available from different suppliers.

N-hydroxyoctanamide (CAS-Nr. 7377-03-9) is commercially readily available.

The hyperbranched copolymer (HBC) is preferably prepared by the following consecutive steps of:
 a1) polymerizing the monomers (i) and monomers (ii) and monomers (iii) to yield a polyesteramide having terminal dimethyl amino groups of the formula

a2) quaternization of the dimethyl amino groups of the polyesteramide of step a1) by 2-chloroacetate, particularly by sodium 2-chloroacetate.

Details for the polymerization step a1) to yield the respective polyesteramide having terminal dimethyl amino groups of the formula

are disclosed for example by EP 2 794 729 B1.

Preferably in the polymerization step a1) the monomer (iii) is added to a mixture of monomers (ii) and (iii) under stirring, followed by heating.

Details of the quaternization step a2) are disclosed as well by EP 2 794 729 B1. Therefore, the entire content of EP 2 794 729 B1 is hereby incorporated by reference.

It is preferred that the molar ratio of the monomers (i) to monomers (ii) is between 5:1 and 0.5:1, particularly between 4:1 and 1:1, preferably between 3:1 and 3:2.

It is further preferred that the molar ratio of the monomers (i) to monomers (iii) is between 5:1 and 0.5:1, particularly between 3:1 and 1:1, preferably between 2.5:1 and 1.1:1.

The hyperbranched copolymer (HBC) has preferably a number average molecular weight $M_n$ of between 1400 and 3000 g/mol, preferably between 2100 and 2400 g/mol.

Preferably, the hyperbranched copolymer (HBC) is polyquaternium-110, also identified by CAS Number 1323977-82-7.

The composition comprises 1,3-propanediol and/or N-hydroxyoctanamide.

In one preferred embodiment, the composition comprises 1,3-propanediol and not N-hydroxyoctanamide. In another preferred embodiment, the composition comprises N-hydroxyoctanamide and not 1,3-propanediol.

In a still another preferred embodiment, the composition comprises both 1,3-propanediol and N-hydroxyoctanamide.

It is preferred that the composition comprises 1,3-propanediol and N-hydroxyoctanamide. In the case of mutual presence of comprises 1,3-propanediol and N-hydroxyoctanamide, it is preferred that the weight ratio of 1,3-propanediol to N-hydroxyoctanamide is >1:1, particularly >3:1. In a very preferred embodiment the composition comprises a mixture of 1,3-propanediol and N-hydroxyoctanamide, as commercially available under the tradename Zeastat™ antimicrobial agent from Inolex.

The weight ratio of said hyperbranched copolymer (HBC) and 1,3-propanediol and/or N-hydroxyoctanamide is preferably in the range of between 1:30 and 30:1, more preferred between 1:20-20:1, even more preferred between 1:10 and 10:1.

In a preferred embodiment the weight ratio of said hyperbranched copolymer (HBC) and 1,3-propanediol and/or N-hydroxyoctanamide is larger than 1:1.

In one embodiment of the invention, the composition of hyperbranched copolymer (HBC) and 1,3-propanediol and/or N-hydroxyoctanamide is used as an antimicrobial agent mixture. Such an antimicrobial agent mixture can be added to any other composition to improve its resistance against microorganisms. Typically, the amounts of hyperbranched copolymer (HBC) and 1,3-propanediol and/or N-hydroxyoctanamide in such an antimicrobial agent mixture is considerable, particularly the amounts of the hyperbranched copolymer (HBC) and 1,3-propanediol and/or N-hydroxyoctanamide is more than 10, particularly more than 30, preferably more than 50, % by weight based on the weight of the antimicrobial agent mixture. It is even possible that such an antimicrobial agent mixture consists of hyperbranched copolymer (HBC) and 1,3-propanediol and/or N-hydroxyoctanamide. Additionally, the antimicrobial agent mixture may also contain further antimicrobial agents.

The composition may additionally comprise at least a further antimicrobial agent. Antimicrobial agents are known as such to the person skilled in the art. The field of use, however, limits the choice of antimicrobial agents which are mainly due particularly to regulatory issues. In the field of food and cosmetics the choice of antimicrobial agents is rather limited.

Therefore, preferred antimicrobial agents suitable for this invention, are antimicrobial agents which are acceptable in the field of food and cosmetics.

In one of the preferred embodiments the antimicrobial agent is selected from the group consisting of:
monoesters or monoethers of glycerol;
salts or esters of aromatic acids;
alkylarylic alcohols;
phenolic ether alcohols;
hydroxyacetophenone
aliphatic diols; and
hydroxamic acids.

Preferred monoesters or monoethers of glycerol are those of formula (I)

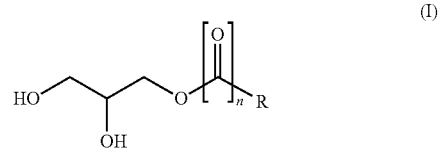

wherein R is a $C_5$-$C_{10}$ alkyl group or $C_5$-$C_{10}$ cyclo alkyl group, preferably a $C_6$-$C_9$ alkyl group or a $C_6$-$C_9$ cyclo alkyl group, more preferably a $C_6$ alkyl group or a $C_8$ alkyl group or a $C_6$ cyclo alkyl group;
and wherein n is either 1 or 0, preferably 0.

In case, where n=0, R is preferably cyclohexyl or n-octyl or n-hexyl or a branched octyl group, preferably an n-hexylgroup or an ethylhexyl group, more preferably a 2-ethylhexyl group. A preferred embodiment is glyceryl caprylate.

In case, where n=1, R is preferably a branched or unbranched saturated or olefinically unsaturated heptyl or nonyl group, preferably a saturated or olefinically unsaturated heptyl or nonyl group, more preferably n-octyl or n-nonyl group, most preferred n-nonyl group.

The monoester or monoethers of glycerol of the formula (I) is preferably selected from the group consisting of cyclohexyl glycerin, hexyl glycerine, ethylhexyl glycerine, glyceryl caprate and glyceryl caprylate, more preferably, hexyl glycerine, ethylhexyl glycerine or glyceryl caprate, most preferably ethylhexyl glycerine or hexyl glycerine. In the most preferred embodiment compound of the formula (I) is 3-(2-ethylhexyloxy)-1,2-propandiol.

Preferred salts of aromatic acids are salts of benzoic acid. Preferred salts are salts of potassium or sodium, preferably sodium salts. Preferred esters of aromatic acids Preferred esters of aromatic acids are alkylesters, particularly $C_1$-$C_6$ alkyl esters of benzoic acid.

Most preferred salts or esters of aromatic acids is sodium benzoate.

Preferred alkylarylic alcohols are alcohols which have a $C_1$-$C_6$ alkylene group, preferably a methylene group, between the hydroxyl group and the aromatic part of the alkylarylic alcohols. Benzyl alcohol is the most preferred alkylarylic alcohols.

Phenolic ether alcohols are alcohols which comprise an alcoholic hydroxyl group as well as an ether of a phenol. The aromatic ring of the phenol is optionally substituted. The ether oxygen and the hydroxyl group are preferably separated by a $C_2$-$C_4$ alkylene group, preferably by an ethylene group. Phenoxyethanol is the most preferred phenolic ether alcohol.

The preferred hydroxyacetophenone is p-hydroxyacetophenone.

Aliphatic diols are alkanes which have 2 hydroxyl groups. These hydroxyl groups are preferably separated by a linear or branched $C_2$-$C_{10}$ alkylene group.

Preferred hydroxamic acids are hydroxamic acids of a saturated $C_3$-$C_{12}$ alkanoic acid. Preferred hydroxamic acid is N-hydroxyoctanamide (=caprylhydroxamic acid).

Preferably the antimicrobial agent is selected from the group consisting of hexyl glycerine, ethylhexyl glycerine or glyceryl caprate, sodium benzoate, benzyl alcohol, phenoxyethanol and N-hydroxyoctanamide.

More preferably, the antimicrobial agent is selected from the group consisting of hexyl glycerine, ethylhexyl glycerine or glyceryl caprate and N-hydroxyoctanamide.

Most preferred, the antimicrobial agent is hexyl glycerine or ethylhexyl glycerine.

In a preferred embodiment the composition is a cosmetic composition.

It is preferred that the amount of 1,3-propanediol and/or N-hydroxyoctanamide is 0.01-6.0% by weight, preferably 0.05-5.0% by weight, more preferably 0.1-3.0% by weight, based on the total weight of the cosmetic composition.

The amount of the hyperbranched copolymer (HBC) in a cosmetic composition is typically between 0.005 and 5.0% by weight, preferably between 0.05 and 5.0% by weight, more preferably between 0.1 and 3.0% by weight, most preferably between 0.5 and 2.5% by weight, based on the total weight of the cosmetic composition.

The cosmetic composition further preferably comprises at least one emulsifier, preferably an anionic emulsifier. Preferably the anionic emulsifier is an anionic emulsifier selected from the group consisting of potassium cetyl phosphate, disodium cetearyl sulfosuccinate, sodium stearoyl glutamate, sodium stearoyl lactylate, glyceryl stearate citrate and sodium cocoyl isethionate.

Potassium cetyl phosphate is commercially available as Amphisol® K at DSM Nutritional Products Ltd Kaiseraugst.

The amount of emulsifier is preferably in the range between 0.1-6.0% by weight, more preferably between 0.25-5.0% by weight, particularly between 0.5-4.0% by weight, based on the total weight of the cosmetic composition.

The composition is preferably sulfate-free.

Hence, the cosmetic composition is preferably particularly free of sulfates of the group consisting of alkyl sulfates, alkyl ether sulfates, alkyl amido ether sulfates, alkylaryl polyether sulfates and monoglycerides sulfate as well as mixtures thereof.

The term "free" as used in the present document, for example in "sulfate-free", is used to mean that the respective substance is only present at amounts of less than 0.5% by weight, particularly less than 0.1% by weight, more particularly below 0.05% by weight, relative to the weight of the composition. Preferably, "free" means that the respective substance is completely absent in the composition.

The term "sulfate-free" is used in the present document to mean that the composition is free of any anionic tenside having a terminal anionic group of the formula

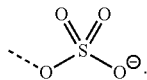

The cosmetic composition is preferably free of cationic emulsifiers. Typical example for such cationic emulsifiers are isostearamidopropyl dimethylamine, stearalkonium chloride, stearamidoethyl diethylamine, behentrimonium methosulfate, behenoyl PG-trimonium chloride, cetrimonium bromide, behenamidopropyl dimethylamine behenate, brassicamidopropyl dimethylamine, stearamidopropyl dimethylamine stearate, cocamidopropyl PG-dimonium chloride, distearoylethyl hydroxyethylmonium methosulfate, dicocoylethyl hydroxyethylmonium methosulfate, distearoylethyl dimonium chloride, shea butteramidopropyltrimonium chloride, behenamidopropyl dimethylamine, brassicyl isoleucinate esylate, acrylamidopropyltrimonium chloride/acrylates copolymer, linoleamidopropyl ethyldimonium ethosulfate, dimethyl lauramine isostearate, isostearamidopropyl laurylacetodimonium chloride, particularly behentrimonium chloride, distearyldimonium chloride, cetrimonium chloride, steartrimonium chloride, and palmitamido-propyltrimonium chloride.

The cosmetic composition further may comprise cosmetic carriers, excipients and diluents as well as additives and active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

Such possible ingredients of the cosmetic composition are particularly enhance the performance and/or consumer acceptability such as preservatives, antioxidants, fatty substances/oils, thickeners, softeners, light-screening agents, moisturizers, fragrances, co-surfactants, fillers, sequestering agents, cationic-, nonionic- or amphoteric polymers or mixtures thereof, acidifying or basifying agents, viscosity modifiers, and natural hair nutrients such as botanicals, fruit extracts, sugar derivatives and/or amino acids or any other ingredients usually formulated into cosmetic compositions. The necessary amounts of the adjuvants and additives can, based on the desired product, easily be chosen by a person skilled in the art in this field and will be illustrated in the examples, without being limited hereto.

The additional ingredients can either be added to the oily phase, the aqueous phase or separately as deemed appropriate.

In an advantageous embodiment, the compositions according to the present invention comprise from 50% to 99%, preferably from 60% to 98%, more preferably from 70% to 98%, such as in particular from 80% to 95% of a carrier, based on the total weight of the cosmetic composition.

In a particular advantageous embodiment, the carrier consists furthermore of at least 40 wt. %, more preferably of at least 50 wt.-%, most preferably of at least 55 wt.-% of water, such as in particular of 55 to 90 wt.-% of water.

Furthermore, it is preferred that the cosmetic composition comprises at least one UV filter. The UV filter may be a liquid or solid UV filter. The UV filter may be a UV-A or UV-B filters.

Suitable liquid UV-filter absorb light in the UVB (280-315 nm) and/or UVA (315-400 nm) range and are liquid at ambient temperature (i.e. 25° C.). Such liquid UV-filter are well known to a person in the art and encompass in particular cinnamates such as e.g. octyl methoxycinnamate (PARSOL® MCX) and isoamyl methoxycinnamate (Neo Heliopan® E 1000), salicylates such as e.g. homosalate (3,3,5 trimethylcyclohexyl 2-hydroxybenzoate, PARSOL® HMS) and ethylhexyl salicylate (also known as ethylhexyl salicylate, 2 ethylhexyl 2-hydroxybenzoate, PARSOL® EHS), acrylates such as e.g. octocrylene (2 ethylhexyl 2-cyano-3,3-diphenylacrylate, PARSOL® 340) and ethyl 2-cyano-3,3 diphenylacrylate, esters of benzmalonic acid such as in particular dialkyl benzalmalonates such as e.g. di (2-ethylhexyl) 4-methoxybenzalmalonate and polysilicone 15 (PARSOL® SLX), dialkylester of naphthalates such as e.g. diethylhexyl 2,6-naphthalate (Corapan® TQ), syringylidene malonates such as e.g. diethylhexyl syringylidene malonate (Oxynex® ST liquid) as well as benzotriazolyl dodecyl p-cresol (Tinoguard® TL) as well as benzophenone-3 and drometrizole trisiloxane.

Particular advantageous liquid UV-filter are octyl methoxycinnamate, homosalate, ethylhexyl salicylate, octocrylene, diethylhexyl 2,6-naphthalate, diethylhexyl syringylidene malonate, benzotriazolyl dodecyl p-cresol, benzo-phenone-3, drometrizole trisiloxane, Polysilicone-15 as well as mixtures thereof.

Suitable solid UV-filter absorb light in the UVB and/or UVA range and are solid at ambient temperature (i.e. 25° C.). They are particularly solid organic UV filters. Particularly suited solid UV-filters are of the group consisting of bis-ethyl-hexyloxyphenol methoxyphenyl triazine, butyl methoxydibenzoyl methane, methylene bis-benzotriazolyl tetramethylbutylphenol, diethylamino hydroxybenzoyl hexyl benzoate, ethylhexyl triazone, diethylhexyl butamido triazone and 4-methylbenzylidene camphor.

The amount of an individual organic UV filter is preferably in the range of 0.1 to about 6% by weight, preferable in the range of 0.5 to 5% by weight, most preferably in the range of 1 to 4% by weight, based on the total weight of the cosmetic composition.

In case of a sun care composition, the total amount of organic UV filter (s) depends strongly on the targeted UV protection of said composition and is typically in the range of between 1 to 50% by weight, preferably between 5 to 40% by weight, based on the total weight of said composition.

A sun creme with an SPF 15 (SPF=sun protection factor), for example, comprises preferably a total amount of organic UV filter (s) of between 4 to 20% by weight, more preferably between 7 and 15% by weight, based on the total weight of said composition.

A sun creme with an SPF 30, for example, comprises preferably a total amount of organic UV filter (s) of between 10 to 40% by weight, more preferably between 15 and 25% by weight, based on the total weight of said composition.

A sun creme with an SPF 50, for example, comprises preferably a total amount of organic UV filter (s) of between 15 to 50% by weight, more preferably between 20 and 40% by weight, based on the total weight of said composition.

Particularly suitable thickeners in all embodiments of the present invention are xanthan gum, gellan gum and/or carboxymethylcellulose. Most preferably in all embodiments of the present invention the thickener is xanthan gum or gellan gum. Further suitable thickeners are polyacrylates such as commercially available under the trade name Carbomer, or acrylate/C10-30 alkyl acrylate crosspolymers or salts of polyacrylic acid or polyacrylamides.

Such thickener(s) are preferably used in an amount (total) selected in the range from 0.1 to 1 wt.-%, more preferably in an amount of 0.1 to 0.5 wt.-%, based on the total weight of the cosmetic composition.

It is preferred that the composition is free of polyvinylpyrrolidones (PVP), particularly free of alkylated polyvinylpyrrolidiones, such as copolymers of N-vinyl-pyrrolidones and hexadecane or eicosene, e.g. as commercially available as Antaron V-216 or Antaron V-220.

The cosmetic compositions according to the invention in general have a pH in the range from 3 to 10, preferably a pH in the range from 4 to 8 and most preferably a pH in the range from 4 to 7.5. The pH is adjusted by methods known to a person skilled in the art, e.g. by using an acid such as a hydroxy acid including glycolic acid, lactic acid, malic acid, citric acid and tartaric acid or a base such as e.g. sodium or potassium hydroxide or ammonium hydroxide as well as mixtures thereof.

Preferably, in the compositions according to the invention citric acid in an amount of at least 0.0001 wt.-%, such as e.g. in an amount of 0.01-1 wt.-%, in particular in an amount of 0.01 to 0.5 wt.-% is used for pH adjustment.

The cosmetic composition is preferably sulfate-free and/or free of para-bens, and/or silicon oils and/or silicone surfactants and/or methylisothiazolidine and/or free of polyvinylpyrrolidones (PVP), particularly free of alkylated polyvinylpyrrolidiones.

The cosmetic composition is preferably a topical composition.

The term "topical" as used herein is understood here to mean external application to keratinous substances, which are in particular the skin, scalp, eyelashes, eyebrows, nails, mucous membranes and hair, preferably the skin.

As the topical compositions are intended for topical application, it is well understood that they comprise a physiologically acceptable medium, i.e. a medium compatible with keratinous substances, such as the skin, mucous membranes, and keratinous fibres. In particular, the physiologically acceptable medium is a cosmetically acceptable carrier.

The term "cosmetically acceptable carrier" refers to all carriers and/or excipients and/or diluents conventionally used in cosmetic compositions such as in particular in sun care products.

Preferably the cosmetic composition is a skin care composition.

In a further embodiment, the cosmetic composition is a decorative preparation or a functional preparation.

Examples of skin care compositions are, in particular, light protective composition, anti-ageing composition, compositions/preparations for the treatment of photo-ageing, body oils, body lotions, body gels, treatment creams, skin protection ointments, skin powders, moisturizing gels, moisturizing sprays, face and/or body moisturizers, skin-tanning preparations (i.e. compositions for the artificial/sunless tanning and/or browning of human skin), for example self-tanning creams as well as skin lightening compositions.

Examples of functional preparations are cosmetic compositions containing active ingredients such as hormone preparations, vitamin preparations, vegetable extract preparations, anti-ageing preparations, and/or antimicrobial (antibacterial or antifungal) preparations without being limited thereto.

The cosmetic composition is preferably a skin care composition.

In a particular embodiment, the cosmetic composition is a sun care composition. Sun care compositions are light-protective composition (sun care products), such as sun protection milks, sun protection lotions, sun protection creams, sun protection oils, sun blocks or day care creams with a SPF (sun protection factor). Sun protection creams, sun protection lotions, sun protection milks and sun protection compositions are of particular interest.

The cosmetic compositions according to the present invention may be in the form of a suspension or dispersion in solvents or fatty substances, or alternatively in the form of an emulsion or micro emulsion (in particular of oil-in-water (O/W-) or water-in-oil (W/O-)type, silicone-in-water (Si/W-) or water-in-silicone (W/Si-)type, PIT-emulsion, multiple emulsion (e.g. oil-in-water-in oil (O/W/O-) or water-in-oil-in-water (W/O/W-)type), pickering emulsion, hydrogel, alcoholic gel, lipogel, one- or multiphase solution or vesicular dispersion or other usual forms, which can also be applied by pens, as masks or as sprays.

Preferred cosmetic compositions in all embodiments of the present invention are emulsions which contain an oily phase and an aqueous phase such as in particular O/W, W/O, Si/W, W/Si, O/W/O, W/O/W multiple or a pickering emulsions.

The total amount of the oily phase present in such emulsions is preferably at least 10 wt.-%, such as in the range from 10 to 60 wt.-%, preferably in the range from 15 to 50 wt.-%, most preferably in the range from 15 to 40 wt.-%, based on the total weight of the cosmetic composition.

The amount of the aqueous phase present in such emulsions is preferably at least 20 wt. %, such as in the range from 40 to 90 wt.-%, preferably in the range from 50 to 85 wt.-%, most preferably in the range from 60 to 85 wt.-%, based on the total weight of the cosmetic composition.

The cosmetic compositions can be in the form of a liquid, lotion, a thickened lotion, a gel, a cream, a milk, an ointment or a paste.

More preferably, the cosmetic compositions according to the present invention are in the form of an oil-in-water (O/W) emulsion comprising an oily phase dispersed in an aqueous phase in the presence of an O/W-respectively Si/W-emulsifier. The preparation of such O/W emulsions is well known to a person skilled in the art.

The compositions in form of O/W emulsions according to the invention can be provided, for example, in all the formulation forms for O/W emulsions, for example in the form of serum, milk or cream, and they are prepared according to the usual methods. The compositions which are subject-matters of the invention are preferably intended for topical application and can in particular constitute a dermatological or cosmetic composition, for example intended for protecting human skin against the adverse effects of UV radiation (antiwrinkle, anti-ageing, moisturizing, anti-sun protection and the like).

It is preferred that the cosmetic composition is a shampoo or a hair conditioner.

It is preferred that the cosmetic composition is a hair care composition.

It is preferred that the cosmetic composition is a shampoo or a hair conditioner.

It is further preferred, that the cosmetic composition is a topical composition applied to the human skin, scalp and/or hair.

It has been surprisingly found that hyperbranched copolymer (HBC) increases the antimicrobial action of antimicrobial agents in cosmetic compositions.

Hence, a further aspect of the present invention relates to the use of a hyperbranched copolymer (HBC) of the monomers
(i) dodecenyl succinic acid anhydride
(ii) diisopropanol amine
(iii) bis-dimethylaminopropyl amine
having terminal groups of the formula

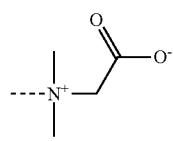

and having a molecular weight Mn of between 1200 and 4000 g/mol; to enhance the antimicrobial action of 1,3-propanediol and/or N-hydroxyoctanamide.

Antimicrobial action has been observed particularly against the microorganisms which are selected from the group consisting *Kocuria rhizophila, Staphylococcus aureus, Enterobacter gergoviae, Escherichia coli, Klebsiella pneumoniae, Pseudomonas aeruginosa, Pseudomonas fluorescens, Pseudomonas putida, Aspergillus brasiliensis, Penicillium pinophilum* and *Candida albicans*, particularly against *Escherichia coli*.

The use of a hyperbranched copolymer (HBC) to enhance the antimicrobial action of 1,3-propanediol and/or N-hydroxyoctanamide can take place both in the cosmetic sense as well as in the pharmaceutical sense It is preferred that the use is a non-therapeutic use.

In a cosmetic composition the use the non-therapeutic use is preferably a cosmetic use, such as for maintenance of skin homeostasis and/or balancing the skin microbiome and/or hair microbiome.

It has been observed that, when adding the above hyperbranched copolymer (HBC) to cosmetic compositions which comprises 1,3-propanediol and/or N-hydroxyoctanamide, the antimicrobial action is increased significantly. In other words, by adding additionally the hyperbranched copolymer (HBC) to a cosmetic composition, which comprises 1,3-propanediol and/or N-hydroxyoctanamide, a smaller number of microbes are observed to grow than without the use of said hyperbranched copolymer (HBC). The above hyperbranched copolymer (HBC) has a synergistic effect on the antimicrobial action of 1,3-propanediol and/or N-hydroxyoctanamide in a composition, particularly in a cosmetic composition.

This is very advantageous also in such a way that the amount of 1,3-propanediol and/or N-hydroxyoctanamide can be reduced by adding the effective amount of the above hyperbranched copolymer (HBC) to maintain the same antimicrobial action.

It has been further observed that the antimicrobial action is particularly pronounced in an aqueous phase. This is very advantageous as it is known that it is typically the water phase of a product which is most susceptible to microbial growth.

EXAMPLES

The present invention is further illustrated by the following experiments. These examples are illustrative only and are not intended to limit the scope of the invention in any way.

Preparation of Hyperbranched Copolymer (HBC1)

The hyperbranched copolymer HBC1 of the monomers dodecenyl succinic acid anhydride and diisopropanol amine and bis-dimethylaminopropyl amine has been prepared according to example 3 in EP 2 794 729 B1 using 237.59 g of N,N-bis(N'N'-dimethylaminopropyl)amine and 112.6 g diisopropanol amine and 426.89 g of dodecenylsuccinic anhydride. After heating and vacuum, the residual carboxylic acid content of <0.3 meq/g (tritrimetrical analysis) AV=9.8 mg KOH/g and amine content of 2.99 meq/g (tritrimetrical analysis) and a molecular weight Mn=2240 Da was obtained. This product has been reacted with sodium chloroacetate in water and stirred at 80° C. until $^1$H-NMR analysis shows a complete conversion of the chloroacetate to obtain the hyperbranched copolymer HBC1 which has terminal groups of the formula

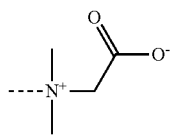

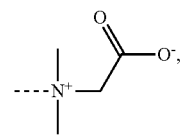

and a molecular weight Mn of 2.3 kDa.

The hyperbranched copolymer HBC1 was used as a 50% solution in water in the following experiments. The amounts indicated in table 1 are based on the amount of polymer.

Testing of Antimicrobial Action (24 Hours Challenge Test)

Since it is known that typically a water phase of a product is most susceptible to microbial growth, the antimicrobial efficacy has been assessed in analogy to the regulatory challenge test method (NF EN ISO11930) for an aqueous solution.

Thus, a solution of HPC1 and/or 1,3-propanediol and/or N-hydroxy-octanamide in an amount as indicated in table 1 were prepared under sterile conditions. For this, it was solubilized in physiological serum with 0.85 wt.-% NaCl. The solutions were deposed in 96-deep well plates (1.6 ml/well). The wells were contaminated with *Escherichia coli* or *Aspergillus brasiliensis*, at $6.3*10^5$ or $4.5*10^4$ cfu/ml, respectively. After the contamination each well was thoroughly mixed to ensure a homogeneous distribution of the microorganism. Then each plate was incubated at 22° C. for 24 h. The counting of the (remaining) population was carried out 24 h after contamination and reported in table 1.

TABLE 1

Antimicrobial action in the 24 hours screen test with *E.coli*. n.m.: not measured.

| | Ref. 1 | Ref. 2 | Ref. 3 | 1 | Ref. 4 | 2 | Ref. 5 | 3 |
|---|---|---|---|---|---|---|---|---|
| HPC1 [wt. %] | | 0.5 | | 0.5 | | 0.5 | | 0.5 |
| 1,3-propanediol [wt. %] | | | 1.0 | 1.0 | | | | |
| Zeastat(1,3-propanediol/N-hydroxy-octanamide)[wt. %] | | | | | 0.3 | 0.3 | | |
| N-hydroxy-octanamide [wt. %] | | | | | | | 0.02 | 0.02 |
| Colony counts after 24 h [cfu/ml] with *E. coli*. | 1'000'000 | <1'000'000 | 1'000'000 | 4'000 | 700'000 | 0 | 700'000 | 400'000 |
| Colony counts after 24 h [cfu/ml] with *Aspergillus brasiliensis*. | 45'000 | 700 | n.m. | n.m. | n.m. | n.m. | 700 | 100 |

The results of table 1 clearly show the effect that these specific copolymers, i.e. the hyperbranched copolymers, increase the antimicrobial action of 1,3-propanediol and/or N-hydroxyoctanamide. This effect is synergistic.

It has been observed that HPC1 and 1,3-propanediol and/or N-hydroxyoctanamide, particularly combined with N-hydroxyoctanamide, show in diverse cosmetic compositions such as shampoo or o/w skin care emulsions an increased antimicrobial effect.

The invention claimed is:

1. A composition comprising:
   (a) a hyperbranched copolymer (HBC) of the monomers:
      (i) dodecenyl succinic acid anhydride;
      (ii) diisopropanol amine; and
      (iii) bis-dimethylaminopropyl amine; wherein the HBC has a molecular weight Mn of between 1200 and 4000 g/mol, and terminal groups of the formula:
   (b) 1,3-propanediol, and
   (c) N-hydroxyoctanamide.

2. The composition according to claim 1 wherein the HBC is prepared by the consecutive steps of:
   A1) polymerizing the monomers (i), (ii) and (iii) to yield a polyesteramide having terminal dimethylamino groups of the formula

and thereafter and a2) conducting quaternization of the dimethyl amino groups of the polyesteramide of step a1) by 2-chloroacetate.

3. The composition according to claim 1, wherein the molar ratio of the monomers (i) to the monomers (ii) is between 5:1 and 0.5:1.

4. The composition according to claim 1, wherein the molar ratio of the monomers (i) to the monomers (iii) is between 5:1 and 0.5:1.

5. The composition according to claim 1, wherein the HBC has a number average molecular weight $M_n$ of between 1400 and 3000 g/mol.

6. The composition according to claim 1, wherein the hyperbranched copolymer is polyquaternium-110.

7. The composition according to claim 1, wherein weight ratio of the HBC to the 1,3-propanediol and N-hydroxyoctanamide is in a range of between 1:30 and 30:1.

8. The composition according to claim 1, wherein the composition is a cosmetic composition.

9. The cosmetic composition according to claim 8, wherein the amount of the HBC is between 0.005 and 5.0% by weight, based on the total weight of the cosmetic composition.

10. The cosmetic composition according to claim 8, wherein the cosmetic composition is a skin care composition.

11. The cosmetic composition according to claim 8, wherein the cosmetic composition is a hair care composition.

12. The cosmetic composition according to claim 8, wherein the cosmetic composition is a shampoo or a hair conditioner.

13. The cosmetic composition according to claim 8, wherein the cosmetic composition is a topical composition applied to the human skin, scalp and/or hair.

14. The cosmetic composition according to claim 8, wherein the 1,3-propanediol and the N-hydroxyoctanamide are present in a weight ratio of the 1,3-propanediol to the N-hydroxyoctanamide which is greater than 1:1.

15. The cosmetic composition according to claim 14, wherein the weight ratio of the 1,3-propanediol to the N-hydroxyoctanamide is greater than 3:1.

16. A method to enhance antimicrobial action of 1,3-propanediol and N-hydroxyoctanamide, wherein the method comprises:
    (a) providing a hyperbranched copolymer (HBC) of the monomers:
        (i) dodecenyl succinic acid anhydride:
        (ii) diisopropanol amine; and
        (iii) bis-dimethylaminopropyl amine; wherein
    the HBC has a molecular weight Mn of between 1200 and 4000 g/mol and terminal groups of the formula:

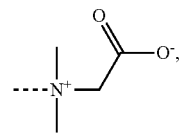

and
    (b) adding an effective amount of the HBC to a mixture of 1,3-propanediol and N-hydroxyoctanamide to enhance the antimicrobial action thereof.

17. The method according to claim 16, wherein the method is non-therapeutic.

18. The method according to claim 16, wherein the 1,3-propanediol and the N-hydroxyoctanamide are present in a weight ratio of the 1,3-propanediol to the N-hydroxyoctanamide which is greater than 1:1.

19. The method according to claim 18, wherein the weight ratio of the 1,3-propanediol to the N-hydroxyoctanamide is greater than 3:1.

* * * * *